United States Patent [19]
Thompson

[11] Patent Number: 5,647,376
[45] Date of Patent: Jul. 15, 1997

[54] SURGICAL DRAPE WITH ELASTICIZED CUFF HAVING FENESTRATION AND SLIT

[75] Inventor: Joseph F. Thompson, Oshkosh, Wis.

[73] Assignee: Allegiance Corporation, McGaw Park, Ill.

[21] Appl. No.: 482,372

[22] Filed: Jun. 7, 1995

[51] Int. Cl.[6] .................................................. A61B 19/08
[52] U.S. Cl. ........................... 128/853; 128/854; 128/855
[58] Field of Search .................................. 128/853, 854, 128/855, 856, 849, 852

[56] References Cited

U.S. PATENT DOCUMENTS

| | | | |
|---|---|---|---|
| 3,930,497 | 1/1976 | Krebs et al. | 128/853 |
| 4,041,942 | 8/1977 | Dougan et al. | 128/853 |
| 4,569,341 | 2/1986 | Morris | 128/853 |
| 5,464,024 | 11/1995 | Mills et al. | 128/853 |
| 5,494,050 | 2/1996 | Reyes | 128/849 |

FOREIGN PATENT DOCUMENTS

81/00086  11/1981  WIPO.

*Primary Examiner*—Mickey Yu
*Assistant Examiner*—Justine Yu
*Attorney, Agent, or Firm*—John R. Flanagan; Robert A. Stenzel

[57] ABSTRACT

A surgical drape for receiving a limb of a patient includes a base sheet having an opening and a passageway extending between the opening and an edge of the base sheet, an elasticized cuff having a central fenestration applied over the opening in the base sheet and attached to the base sheet about the opening in the base sheet, and a separation defined in the cuff extending between the central fenestration and an edge of the cuff and being longitudinally aligned with the passageway of the base sheet for permitting wrapping of the drape around the limb to isolate and form a seal around at least a portion of the limb through the central fenestration of the cuff. The drape may also include a liquid gathering pouch attached to the base sheet and surrounding the cuff and having a layer separate from the base sheet and the cuff to form a pocket therebetween and an opening surrounding the cuff for receiving liquid therein. The drape is further useable in conjunction with an overlay sheet or another drape to close the central fenestration of the cuff with respect to the passageway in the base sheet and to isolate and form a seal around the limb therethrough.

20 Claims, 2 Drawing Sheets

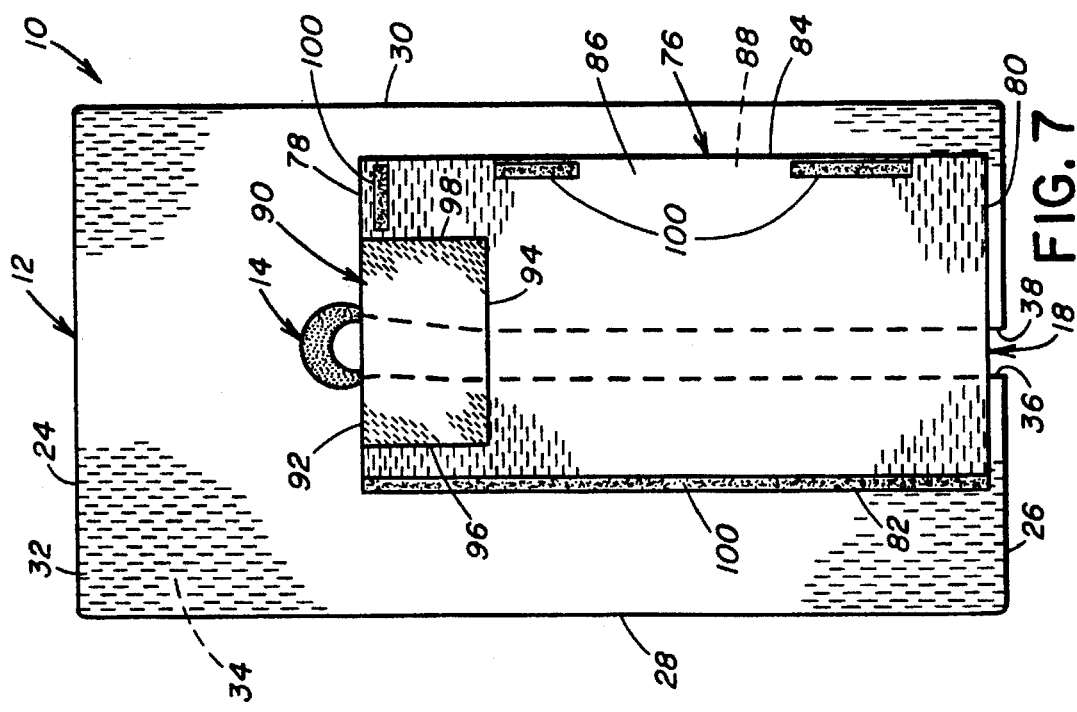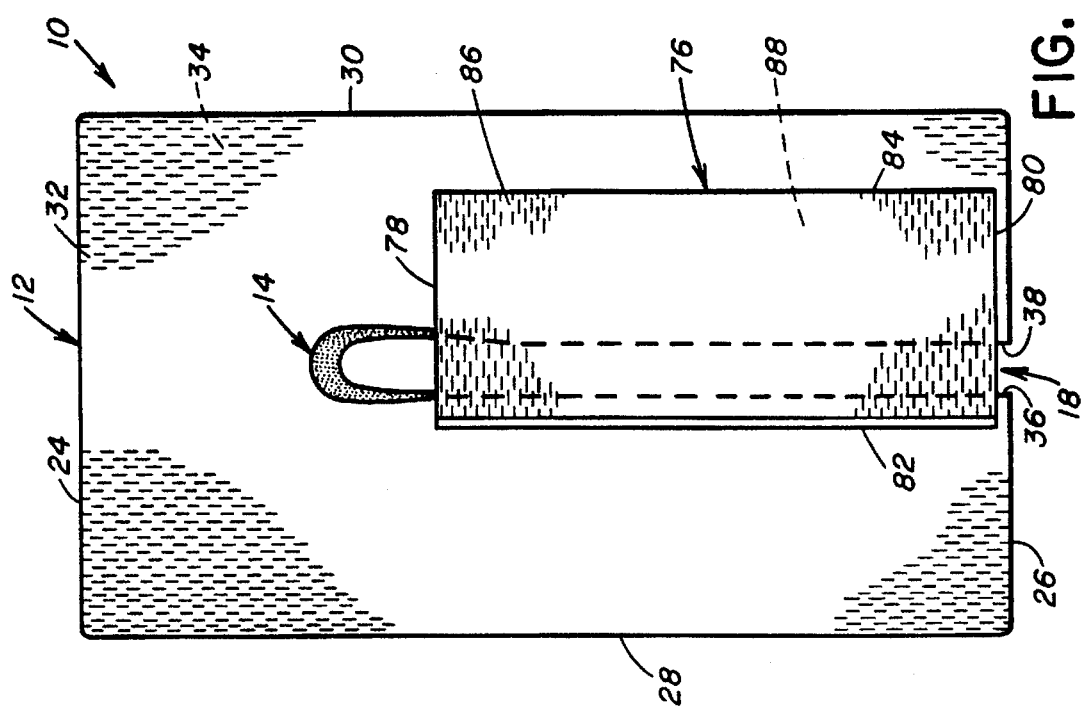

5,647,376

SURGICAL DRAPE WITH ELASTICIZED CUFF HAVING FENESTRATION AND SLIT

BACKGROUND OF THE INVENTION

1. Field of the Invention

The present invention generally relates to surgical draperies for limbs and, more particularly, is concerned with a surgical drape with an elasticized cuff having a fenestration and a slit for receiving a limb of a patient.

2. Description of the Prior Art

A variety of surgical draperies have been developed over the years for covering exposed portions of the body surrounding the area of an incision or wound to prevent contamination. Draperies have been specially designed for use with limbs and other parts of the body. Common elements in many of these draperies include a sheet with a fenestration and a slot for fitting the sheet around a limb. Towel clamps or clips used in surgical procedures or adhesive strips are commonly utilized to secure drapes to one another or, in the case of adhesives, to the skin of the patient.

Representative examples of surgical draperies are disclosed in U.S. Pat. No. 3,930,497 to Krebs et al., PCT App. No. PCT/GB81/00086 to Coates et al. and U.S. Pat. No. 4,569,341 to Morris. The draperies in these patents attempt to overcome problems in the prior art. The Krebs patent addresses the difficulty in completely sealing the area of the incision. Before the Krebs patent, adhesive attachments were used which lacked adjustability for use with a variety of areas of the body and during operations thus making the drapery unable to ensure a complete seal in a variety of situations to prevent contamination. The Krebs patent provides a disposable drape made of a liquid repellant material with a variable U-shaped fenestration and a layer of adhesive surrounding the closed end and at least the sides of the fenestration.

The Coates patent provides a disposable surgical drape having a square web comprising fibers which prevent contamination. To the upper side of this web is secured a smaller square panel of thin, liquid impermeable material which is a plastic film or a plastic-coated nonwoven fabric. The drape is fenestrated with a slot extending to the side edge of the web. Coated on the marginal portions of the material surrounding the fenestration is an adhesive for securing the drape to the patient's body.

The Morris patent addresses the problem in the prior art of there not being an effective means for securing the drape in a proper position around the patient's limb. The use of towel clamps or clips had a tendency to cause perforations in the drape which would permit the penetration of outside liquids. The use of adhesive strips were inadequate to hold the drape in place because the adhesive would not securely bond to the fibrous surface of the drape. The Morris solution was to utilize a plastic film around the fenestration to provide a better surface for bonding of the adhesive to secure an opposing second drape to the first drape so as to isolate the limb of the patient through the fenestration.

A problem exists, however, in these draperies which utilize an adhesive substance. Moisture on the skin of a patient can reduce the strength of the bond between the adhesive and the skin and therefore prevent the formation of a liquid resistant seal. Strips of tape which have a layer of adhesive, for instance, are more vulnerable to delamination from skin in the presence of moisture and swelling which thereby may compromise the liquid barrier.

Further developments utilize elastic borders around the fenestrations. The elasticized fenestrations which are currently produced are circumferentially bounded by the material making up the drape itself and are cut to a predetermined size to fit particular limb shapes and sizes. A problem exists, however, in these drapes which utilize elastic openings in that flexibility in placing the fenestration so as to obtain the exposure needed around a particular limb is limited due to the elastic border completely surrounding the fenestration. Sterile technique may also be compromised because the drape must be slipped over the limb from the end first as there is no separation in the drape to permit wrapping around the limb instead.

Consequently, a need still exists for a surgical drape with overcomes the aforementioned problems in the prior art without introducing new problems in their place.

SUMMARY OF THE INVENTION

The present invention provides a surgical drape with an elasticized cuff having a fenestration and a slit for receiving a limb of a patient designed to satisfy the aforementioned need. The slit in the elasticized cuff of the drape of the present invention has the flexibility necessary for the drape to be used with a variety of limb shapes and sizes. A sterile technique is also maintained by wrapping the drape around the limb rather than slipping the drape over the limb from the end first as is required when there is no separation in the drape to permit such wrapping.

Accordingly, the present invention is directed to a surgical drape for receiving a limb of a patient. The drape comprises: (a) a base sheet having an opening and a passageway extending between the opening and an edge of the base sheet; (b) an elasticized cuff having a central fenestration applied over the opening in the base sheet, the cuff being attached to the base sheet about the opening in the base sheet; and (c) means defining a separation in the cuff extending between the central fenestration and an edge of the cuff, the separation being longitudinally aligned with the passageway of the base sheet for permitting wrapping of the drape around the limb to isolate and form a seal around at least a portion of the limb extending through the central fenestration of the cuff.

More particularly, the base sheet is substantially rectangular in shape and is made substantially of a flexible liquid impermeable material. The passageway of the base sheet is also substantially rectangular in shape and is defined by a pair of spaced interior edges in the base sheet. The opening of the base sheet is defined by opposite side edges spaced apart at a distance greater than the distance between the interior edges defining the passageway of the base sheet.

The elasticized cuff is a layer substantially rectangular in shape and has a width which is greater than the distance between the opposite side edges of the opening of the base sheet. Also, the cuff is made substantially of a flexible liquid impermeable material. The central fenestration of the cuff is generally smaller than the opening of the base sheet. The means defining a separation in the cuff is preferably a slit having a pair of opposite side edges which touch one another so that the passageway of the base sheet is normally closed through the separation means with respect to the central fenestration of the cuff. The separation in the cuff is alternatively a slot having a pair of opposite side edges which are spaced apart from one another so that the passageway of the base sheet is normally open through the separation means with respect to the central fenestration of the cuff.

Furthermore, the surgical drape may also include a liquid gathering pouch made of a layer of substantially a flexible liquid impermeable material attached to the base sheet and having a cutout region therein which generally conforms to the shape of the cuff. The pouch layer is only sealably attached about its outer perimeter to the base sheet and so is separated from the base sheet and the cuff throughout most of its area and particularly about the inner perimeter of the pouch layer to form a pocket therebetween having an opening extending about the cuff for receiving liquid therethrough.

The drape may also include an overlay sheet for attachment to the base sheet adjacent to the passageway therein for covering the passageway of the base sheet and for assisting in isolating and forming a seal around the limb. The overlay sheet may have an upper elastic portion adjacent to the central fenestration of the cuff to provide a more complete seal around the limb. The overlay sheet and the base sheet may have a plurality of complementary patches of mateable hook and loop elements for attachment of the overlay sheet to itself to temporarily expose the passageway in the base sheet. The drape is further useable in conjunction with another drape to enclose the central fenestration of the cuff with respect to the passageway in the base sheet and to isolate and form a seal around the limb therethrough.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 6 is a top plan view of an alternative embodiment of the surgical drape having an elasticized cuff and an overlay sheet attached to the base sheet.

FIG. 7 is a top plan view of another embodiment of the surgical drape having an elasticized cuff and an elasticized overlay sheet attached to the base sheet.

DETAILED DESCRIPTION OF THE INVENTION

Figure 1:
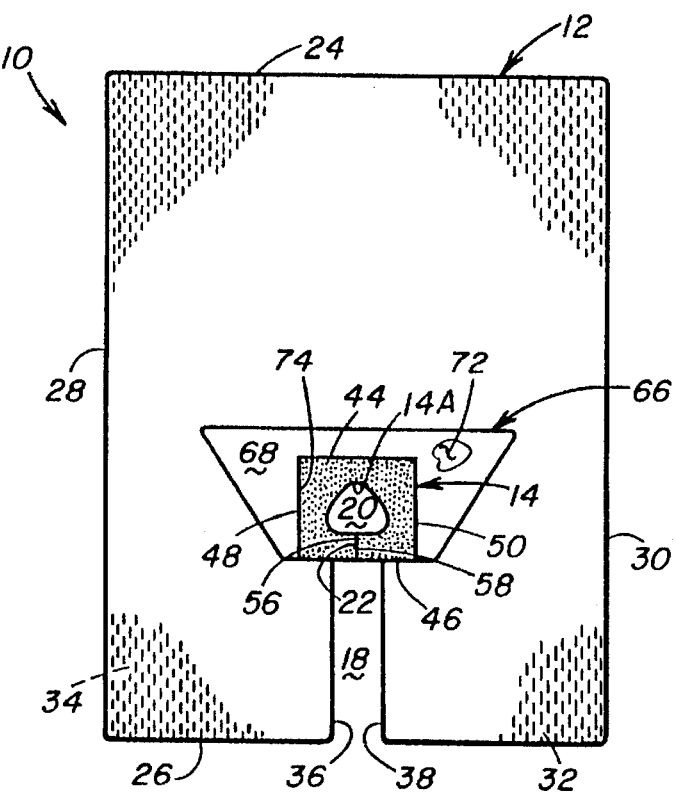
FIG. 1 is a top plan view of a preferred embodiment of a surgical drape with an elasticized cuff for receiving a limb of a patient and a liquid gathering pouch attached to a base sheet of the surgical drape.
Figure 5:
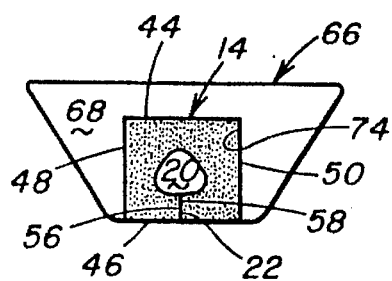
FIG. 5 is a top plan view of the liquid gathering pouch surrounding the elasticized cuff of the surgical drape.

Referring to the drawings and particularly to FIGS. 1 to 5, there is illustrated a surgical drape, generally designated 10, of the present invention for receiving a limb of a patient. Basically, the drape 10 includes a base sheet 12 and an elasticized cuff 14. The base sheet 12 has an opening 16 and a passageway 18 extending between the opening 16 and an edge of the base sheet 12. The elasticized cuff 14 has an internal edge 14A defining a central fenestration 20 and is attached to the base sheet 12 and applied over the opening 16 in the base sheet 12. The cuff 14 about its periphery is attached to the base sheet 12 about and adjacent to all sides of the opening 16 in the base sheet 12 and extends across the opening 16. A separation 22 is defined in the cuff 14, extending between the central fenestration 20 and an edge of the cuff 14. The separation 22 is longitudinally aligned with the passageway 18 of the base sheet 12. The presence and orientation of the separation 22 permits the wrapping of the drape 10 directly around the desired location on the limb (not shown) to isolate and form a seal around at least a portion of the limb extending through the central fenestration 20 of the cuff 14, without first having to slip the top sheet over the limb end first as required in the prior art discussed earlier.

The base sheet 12 of the drape 10 is substantially rectangular in shape and is made substantially of any suitable flexible liquid impermeable material being well-known to those skilled in the art. The base sheet 12 particularly has a top edge 24, a bottom edge 26, a pair of opposing side edges 28 and 30, an upper surface 32, and a lower surface 34. The opening 16 in the base sheet 12 is spaced from each of the edges 24, 26, 28 and 30, whereas the passageway 18 extends between and opens at the opening 16 and the bottom edge 26 of the base sheet 12. The passageway 18 of the base sheet 12 is substantially rectangular in shape and is defined by a pair of spaced interior longitudinal edges 36 and 38 in the base sheet 12. The opening 16 of the base sheet 12 is defined by interior side edges 40 and 42 being spaced apart at a distance greater than the distance between the interior edges 36 and 38 which define the passageway 18 of the base sheet 12.

The elasticized cuff 14 of the drape 10 is substantially rectangular in shape and substantially smaller than the base sheet 12. The cuff 14 has a width W greater than the distance between the opposite side edges 40 and 42 of the opening 16 of the base sheet 12 and is made substantially of any suitable flexible liquid impermeable material, such as elastomeric films, one example of which being Kraton film. The cuff 14 has a top edge 44, a bottom edge 46, a pair of opposing side edges 48 and 50, an upper surface 52, and a lower surface 54. The central fenestration 20 in the cuff 14 is spaced from each of the edges 44, 46, 48 and 50 of the cuff 14. The lower surface 54 of the cuff 14 is applied over the opening 16 on the upper surface 32 of the base sheet 12 and the cuff 14 at its periperhy is attached to the upper surface 32 of the base sheet 12 surrounding and adjacent to all sides of the opening 16. Any suitable means of attachment can be used. Some examples are ultrasonics and adhesive attachment systems. The central fenestration 20 of the cuff 14 is generally smaller than and is contained within the opening 16 in the base sheet 12 such that the elastic material of the cuff 14 adapts it to seal around and conform to the size of the limb of a patient extending through the central fenestration 20 of the cuff 14 and opening 16 of the base sheet 12.

The separation 22 in the cuff 14 extends between the central fenestration 20 and the bottom edge 46 of the cuff 14. The separation 22 is longitudinally aligned with the passageway 18 in the base sheet 12 for receiving the limb therethrough and into the central fenestration 20 in the cuff 14 so as to isolate and form a seal around at least a portion of the limb disposed through the central fenestration 20 of the cuff 14. The separation 22 in the cuff 14 is preferably a slit 22 having a pair of opposite side edges 56 and 58 which touch one another so that the passageway 18 of the base sheet 12 is normally closed with respect to the central fenestration 20 of the cuff 14.

Figure 3:
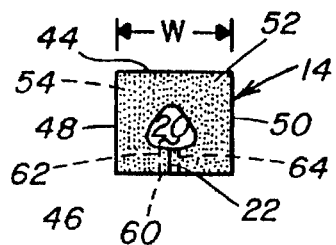
FIG. 3 is a top plan view of the elasticized cuff of the surgical drape.
Figure 4:
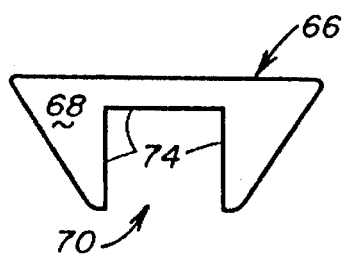
FIG. 4 is a top plan view of the liquid gathering pouch of the surgical drape.
Figure 2:
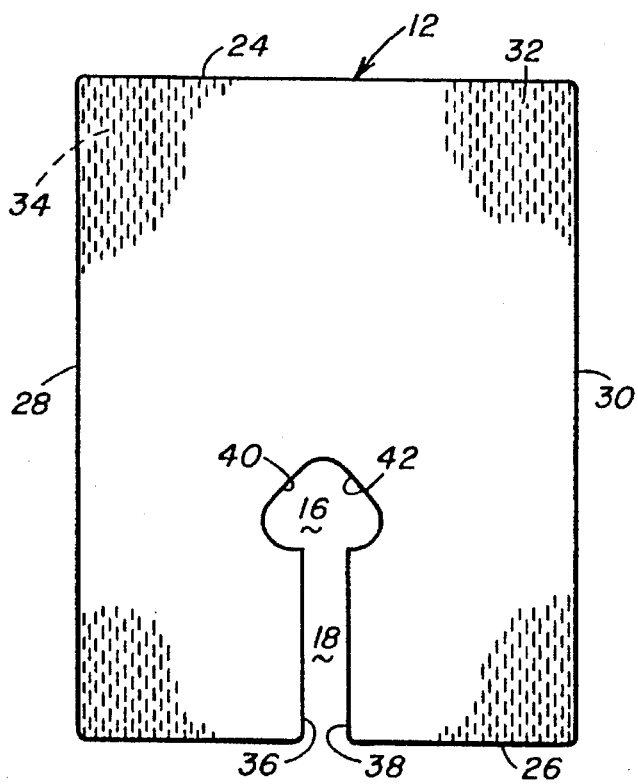
FIG. 2 is a top plan view of the base sheet of the surgical drape.

Alternatively, the separation 22 in the cuff 14 can be a slot 60, as shown particularly in FIG. 3. The slot 60 is defined by a pair of opposite side edges 62 and 64 which are spaced apart from one another so that the passageway 18 of the base sheet 12 is normally open with respect to the central fenestration 20 of the cuff 14.

Optionally, the drape 10 may further include a liquid gathering pouch 66 made substantially of any suitable flexible liquid impermeable material. The pouch 66 is formed by a layer 68 attached by any suitable means to the upper surface 32 of the base sheet 12 and having a cutout region 70 therein which generally conforms to the shape of the cuff 14 by surrounding the top edge 44 and the pair of opposing side edges 48 and 50 of the cuff 14. The layer 68 is only sealably attached about its outer perimeter to the base sheet 12 and so is separated from the base sheet 12 and the cuff 14 throughout most of the area of the layer 68 and particularly about an inner perimeter of the layer 68 defined by the cutout 70 to form a pocket 72 therebetween having an opening 74 extending about the cuff 14 for receiving liquid therethrough. The pouch 66 can be adapted to release liquid trapped in the pocket 72 thereof in a controlled manner such as by a suction or drain tube (not shown) attached to the pouch 66.

Referring now to FIGS. 6 and 7, the drape 10 may further include an overlay sheet 76 being substantially rectangular in shape and made substantially of any suitable flexible liquid impermeable material. The overlay sheet 76 is attached to the upper surface 32 of the base sheet 12 adjacent to the passageway 18 and is adapted for covering the passageway 18 of the base sheet 12 to assist in isolating and forming a seal around the limb therethrough. The overlay sheet 76 has a top edge 78, a bottom edge 80, a pair of opposite side edges 82 and 84, an upper surface 86 and a lower surface 88. The portion of the overlay 76 to the right of the passageway 18, as viewed in FIGS. 6 and 7, is attached to the upper surface 32 of the base sheet 12 so that the overlay 76 normally function as a flap covering the passageway 18 but can be folded to the right to temporarily open and expose the passageway 18 leading to the fenestration 20.

As shown in FIG. 7, the overlay sheet 76 may also have an elastic portion 90 substantially rectangular in shape and made substantially of the same material as the cuff 14 and being attached by the same means to the portions of the overlay sheet 76 surrounding the elastic portion 90. The elastic portion 90 also is disposed adjacent to the central fenestration 20 of the cuff 14 for covering the upper portion of the passageway 18 adjacent to the central fenestration 20 of the base sheet 12 to further help isolate and seal around the limb extending therethrough. Thus, the elastic portion 90 in combination with the central fenestration 20 of the cuff 14 provides a more complete seal around the limb. The elastic portion 90 has a top edge 92, a bottom edge 94 and a pair of opposite side edges 96 and 98. The top edge 92 of the elastic portion 90 forms a continuation of the top edge 78 of the overlay sheet 76 while the bottom edge 94 of the elastic portion 90 is spaced substantially inwardly from the bottom edge 80 of the overlay sheet 76. The opposite side edges 96 and 98 of the elastic portion 90 are spaced inwardly from the opposite side edges 82 and 84 of the overlay sheet 76.

For folding over the overlay sheet 76 to expose the passageway 18, the overlay sheet 76 may further have a plurality of complementary patches 100 of mateable hook and loop fastening elements applied on the upper surface 86 thereof. The patches 100 are generally located along the top edge 78 and the opposite side edges 82 and 84 on the upper surface 86 of the overlay sheet 70. These patches can also be employed between the overlay sheet 76 and the base sheet 12 to attached the overlay sheet 76 thereto.

The drape 10 is further useable in conjunction with another drape 10 to enclose the central fenestration 20 of the cuff 14 with respect to the passageway 16 in the base sheet 12 and to isolate and form a seal around the limb therethrough. It is readily apparent that the drape 10 of the present invention when used either alone or with another drape 10 can provide a seal which will function over an anatomically irregular surface which is often the situation in the case of limb surgeries.

It is thought that the present invention and its advantages will be understood from the foregoing description and it will be apparent that various changes may be made thereto without departing from its spirit and scope of the invention or sacrificing all of its material advantages, the form hereinbefore described being merely preferred or exemplary embodiment thereof.

I claim:

1. A surgical drape for receiving a limb of a patient, said drape comprising:
    (a) a base sheet having interior side edges defining an opening and a passageway extending between said opening and an outer edge of said base sheet, said passageway being defined by a pair of spaced apart interior longitudinal edges in said base sheet, said interior side edges defining said opening of said base sheet being spaced apart at a distance greater than the distance between said interior longitudinal edges defining said passageway of said base sheet;
    (b) an elasticized cuff having an internal edge defining a central fenestration in said cuff, said cuff being attached to said base sheet about said opening and extending across said opening in said base sheet such that said internal edge of said cuff is spaced inwardly from said interior side edges of said base sheet and said fenestration of said cuff is smaller in size than and contained within said opening of said base sheet, said cuff being made of an elastic material adapted to seal around and conform the fenestration to the size of a limb of a patient extending through said fenestration of said cuff and opening of said base sheet; and
    (c) means defining a separation in said cuff extending between said central fenestration and an outer edge of said cuff, said separation being longitudinally aligned with said passageway of said base sheet for permitting wrapping of said drape around a limb to isolate and form a seal around at least a portion of the limb extending through said central fenestration of said cuff, said separation defined by a pair of opposite side edges which are spaced apart from one another by a distance less than that spacing apart said interior longitudinal edges in said base sheet.

2. The drape of claim 1 wherein said base sheet is substantially rectangular in shape.

3. The drape of claim 1 wherein said base sheet is made substantially of a liquid impermeable material.

4. The drape of claim 1 wherein said cuff is made substantially of a liquid impermeable material.

5. The drape of claim 1 wherein said means defining a separation in said cuff is a slit having said pair of opposite side edges which touch one another so that said passageway of said base sheet is normally closed through said separation means with respect to said central fenestration of said cuff.

6. The drape of claim 1 wherein said means defining a separation in said cuff is a slot having said pair of opposite side edges which are spaced apart from one another so that said passageway of said base sheet is normally open through said separation means with respect to said central fenestration of said cuff.

7. The drape of claim 1 further comprising:
    (d) an overlay sheet attached to said base sheet adjacent to said passageway therein for covering said passageway of said base sheet to assist in isolating and forming the seal around the limb extending therethrough.

8. The drape of claim 7 wherein said overlay sheet has a plurality of complementary patches of mateable hook and loop fastener elements applied thereon for releasable attachment of said overlay sheet to itself.

9. The drape of claim 7 wherein said overlay sheet has an elastic portion disposed adjacent to said central fenestration of said cuff to provide a more complete seal around the limb.

10. A surgical drape for receiving a limb of a patient, said drape comprising:

(a) a base sheet having an opening and a passageway extending between said opening and an edge of said base sheet;

(b) an elasticized cuff having a central fenestration applied over said opening in said base sheet, said cuff being attached to said base sheet about said opening in said base sheet;

(c) means defining a separation in said cuff extending between said central fenestration and an edge of said cuff, said separation being longitudinally aligned with said passageway of said base sheet for permitting wrapping of said drape around a limb to isolate and form a seal around at least a portion of the limb extending through said central fenestration of said cuff; and (d) a liquid gathering pouch attached on said base sheet and substantially surrounding said cuff so as to form a pocket with said base sheet, said pouch having an opening substantially surrounding said cuff for receiving liquid therethrough and into said pocket of said pouch.

11. The drape of claim 10 wherein said base sheet is made substantially of a liquid impermeable material.

12. The drape of claim 10 wherein said passageway of said base sheet is defined by a pair of spaced interior edges in said base sheet.

13. The drape of claim 12 wherein said opening of said base sheet is defined by opposite side edges spaced apart at a distance greater than the distance between said interior edges defining said passageway of said base sheet.

14. The drape of claim 13 wherein said cuff has a width greater than the distance between said opposite side edges of said opening of said base sheet.

15. The drape of claim 10 wherein said cuff is made substantially of a liquid impermeable material.

16. The drape of claim 10 wherein said central fenestration of said cuff is smaller than said opening of said base sheet.

17. The drape of claim 10 wherein said means defining a separation in said cuff is a slit having a pair of opposite side edges which touch one another so that said passageway of said base sheet is normally closed through said separation means with respect to said central fenestration of said cuff.

18. The drape of claim 10 wherein said means defining a separation in said cuff is a slot having a pair of opposite side edges which are spaced apart from one another so that said passageway of said base sheet is normally open through said separation means with respect to said central fenestration of said cuff.

19. The drape of claim 10 wherein said pouch is made substantially of a liquid impermeable material.

20. The drape of claim 10 wherein said pouch is a layer attached to said base sheet and having a cutout region which generally conforms to the shape of said cuff and is only sealably attached to said base sheet about an outer perimeter of said layer so that said layer is substantially separated from said base sheet and said cuff throughout most of said layer and about an inner perimeter of said layer to form said pocket therebetween having an opening extending about said cuff for receiving liquid therethrough.

* * * * *